United States Patent [19]

Papurt

[11] Patent Number: 5,070,890

[45] Date of Patent: Dec. 10, 1991

[54] MALE CONDOM DEVICE AND METHOD OF USING SAME

[76] Inventor: David M. Papurt, 37 Kinnaird St., Cambridge, Mass. 02139

[21] Appl. No.: 603,244

[22] Filed: Oct. 22, 1990

Related U.S. Application Data

[63] Continuation of Ser. No. 405,340, Sep. 11, 1989, abandoned.

[51] Int. Cl.$^5$ .............................................. A61F 6/04
[52] U.S. Cl. ...................................... 128/844; 128/918
[58] Field of Search ................ 128/842, 844, 79, 918; 604/330, 347–353

[56] References Cited

U.S. PATENT DOCUMENTS

| | | | |
|---|---|---|---|
| D. 246,117 | 10/1977 | Okamoto | 128/79 |
| D. 246,118 | 10/1977 | Okamoto | D24/99 |
| D. 246,119 | 10/1977 | Okamoto | D24/99 |
| D. 252,949 | 9/1979 | Okamoto | D24/99 |
| D. 254,808 | 4/1980 | Meldahl | D24/99 |
| 807,798 | 3/1905 | Wood | 168/21 |
| 947,725 | 1/1910 | Yates | 604/353 |
| 2,123,343 | 7/1938 | Rightsell | 128/842 |
| 2,591,783 | 4/1952 | Craddock | 604/353 |
| 3,037,508 | 6/1962 | Friedman | 128/844 |
| 3,536,066 | 10/1970 | Ludwig | 128/844 |
| 3,751,254 | 9/1973 | Clark | 128/844 |
| 4,354,494 | 10/1982 | Hogin | 128/844 |
| 4,415,548 | 11/1983 | Reddy | 428/28 |
| 4,590,931 | 5/1986 | Kidwell | 128/162 |
| 4,664,104 | 5/1987 | Jaicks | 128/844 |
| 4,735,621 | 4/1988 | Hessel | 604/349 |
| 4,781,709 | 11/1988 | Grubman | 604/349 |
| 4,794,920 | 1/1989 | Robichaud | 128/844 |
| 4,807,611 | 2/1989 | Johnson | 128/844 |
| 4,808,174 | 2/1989 | Sorkin | 604/352 |
| 4,817,593 | 4/1989 | Taller | 128/844 |
| 4,834,113 | 5/1989 | Reddy | 128/844 |
| 4,834,114 | 5/1989 | Boarman | 128/844 |
| 4,840,624 | 6/1989 | Lee | 604/353 |

FOREIGN PATENT DOCUMENTS

| | | | |
|---|---|---|---|
| 0211350 | 6/1909 | Fed. Rep. of Germany | 604/349 |
| 0254211 | 11/1912 | Fed. Rep. of Germany | 604/349 |
| 0267218 | 11/1913 | Fed. Rep. of Germany | 604/349 |
| 0146306 | 6/1936 | Fed. Rep. of Germany | 604/349 |
| 0214764 | 10/1984 | Fed. Rep. of Germany | 604/353 |
| 3606126 | 8/1987 | Fed. Rep. of Germany | 128/79 |
| 0272418 | 3/1951 | Switzerland | 604/349 |

OTHER PUBLICATIONS

Himes, N. E., *Medical History of Contraception*, Schocken Books, 1970, pp. 186–206.
Barlow, D. *Sexually Transmitted Diseases, The Facts*, Oxford University Press, 1979, p. 75.

*Primary Examiner*—Robert A. Hafer
*Assistant Examiner*—Michael Brown

[57] ABSTRACT

The present invention relates to mechanical barrier condom prophylactic and contraceptive devices of tubular construction that have a closed end and an open end. The condom device is a continuous sheath that, when in place over the male genitalia, covers, and conforms to the general shape of, the entire erect penis, including the base of the penis shaft, and the entire scrotum.

22 Claims, 4 Drawing Sheets

MALE CONDOM DEVICE AND METHOD OF USING SAME

This application is a continuation of application Ser. No. 07/405,340, filed Sept. 11, 1989 now abandoned.

BACKGROUND OF THE INVENTION

1. Field of the Invention

The present invention relates to mechanical barrier prophylactic devices for preventing venereal infection and to mechanical barrier contraceptive devices for preventing conception. In particular, the present invention relates to condom or sheath devices.

2. Description of Related Art

Condom barrier prophylactic devices and barrier contraceptive devices are generally known in the overall population, as well as in the art, for their ability to prevent venereal infection and conception.

Condom devices generally are thin walled tubular constructions that have a closed end and an open end. The open end assumes a variety of shapes and configurations. As a consequence different condom devices achieve prophylaxis and contraception at varying levels of effectiveness, cost and convenience.

The more common types, male condoms, are placed on the penis prior to sexual contact. Other types, the so-called female condoms, are positioned intravaginally prior to sexual contact. The present invention is classified as a male condom.

A search of the prior art failed to uncover any prior art reference which discloses the condom device of the present invention. However, several prior art patents and unpatented prior art were uncovered which disclose various condom devices.

For example, U.S. Pat. No. 4,735,621 discloses a female condom that includes a closed end tube with a collar shaped outwardly extending portion at the open end and elastic rings that maintain the position and shape of the device when in use.

U.S. Pat. No. 4,781,709 discloses a male condom that includes a closed end sleeve integral with an elongated sheet at the open end.

U.S. Pat. No. 4,664,104 discloses a condom system that includes cooperatively associated garments worn by the participants.

U.S. Pat. No. 4,834,113 discloses a prophylactic device adapted to be worn by the female and including a flat shield portion that spans the perineum.

U.S. Pat. No. 4,834,114 discloses a female condom that includes a shield coupled to a closed end tube.

The above-described prior art devices are intended to achieve prophylaxis and contraception, but have a number of common disadvantages which limit their convenience and increase their cost. Each device is comprised of or fabricated from more than a single component, making each relatively expensive and inconvenient to use. Further, each device limits the experience of the sexual act to less than that gained by the use of more convenient prophylactic and contraceptive devices.

U.S. Pat. No. 2,123,343 discloses a covering for a body organ comprising a flexible cot secured to the base of, and centrally located within, a fexible disk. This cover provides inferior prophylactic and contraceptive effectiveness due to its unrestrained disk.

Historically, the condom has been in existance for centuries. Himes points out evidence that implies condoms made of animal membrane were employed in Imperial Rome. Linen condoms were described by the Italian anatomist Fallopius in the sixteenth century. The successful vulcanization of rubber in the mid-nineteenth century lowered costs for the condom materially. Modern male condoms are fabricated in a single piece out of latex using automatic machinery.

U.S. Pat. No. 4,415,548 discloses a method for the manufacture of commercially available condoms. U.S. Design Pat. Nos. 252,949; 246,117; 246,118; and 246,119 disclose novelty condoms comparable in shape to commercially available male condom types.

Condoms of this type very often slip off during or following use. The possibility of infection or unwanted conception accompanies this event.

The sore of primary syphilis, or chancre, is usually found on the glans penis. Barlow points out the less common condom chancre found at the base of the shaft of the penis. In such cases the individual has taken the precaution of wearing a commercially available condom, which remained intact and in place, but a syphilis infection initiated on the part of the penis not covered by the condom.

The implication of this last limitation of current condom designs is horrific when viewed in terms of the current AIDS pandemic. Human Immuno Deficiency Virus can pass from female to male, or vice versa, via the unprotected skin at the base of the penis shaft or the scrotum.

OBJECTS

In view of the foregoing limitations and shortcomings of the prior art devices, as well as other disadvantages not specifically mentioned above, it should be apparent that prior to the present invention there existed a need in the art for an improved condom. It is, therefore, a primary object of this invention to fulfill that need by providing an improved condom device.

More particularly, it is an object of the present invention to provide a highly prophylactic condom device that prevents transmission of venereal infections from female to male, or vice versa, via the skin at the base of the penis shaft and the scrotum.

It is another object of the present invention to provide a highly contraceptive condom device that is unlikely to slip off during or following use.

A further object of the present invention is to provide a condom device that is convenient to use.

Yet another object of the present invention is to provide a condom device that is simple and inexpensive to fabricate.

SUMMARY OF THE INVENTION

Briefly described, these and other objects are accomplished according to the invention by providing a male condom device that is placed over the male genitalia prior to sexual contact.

The condom device is a thin walled tubular construction of elastic or inelastic material and has a closed end and an open end. The condom device is a continuous sheath that, when in place, covers, and conforms to the general shape of, the entire erect penis, including the base of the penis shaft and the entire scrotum. The open end may include an integral elastic ring of heavier construction than the thin tubular sheath and may be stretched against the bordering regions of the anatomy. There may also be bonded to the open end a plurality of integral handle elements to be be located on or grasped between the fingers of the hands while placing or removing the condom device. The closed end covering the glans penis may include a smaller diameter, closed tube at the urethra as a receptacle for ejaculate. A second integral elastic ring of heavier construction than the thin tubular sheath that, when in place, is located on the penis shaft near the penis base and is stretched around the penis base may be bonded to the thin tubular sheath.

Venereal disease prophylaxis and contraception is achieved by providing a condom device as described above, and positioning it over the male genitalia prior to sexual contact.

With the foregoing and other objects, advantages and features of the invention that will become hereinafter apparent, the nature of the invention may be more clearly understood by reference to the detailed description of the invention, the appended claims and to the several views illustrated in the attached drawings.

DETAILED DESCRIPTION OF THE PREFERRED EMBODIMENTS

Figure 1:
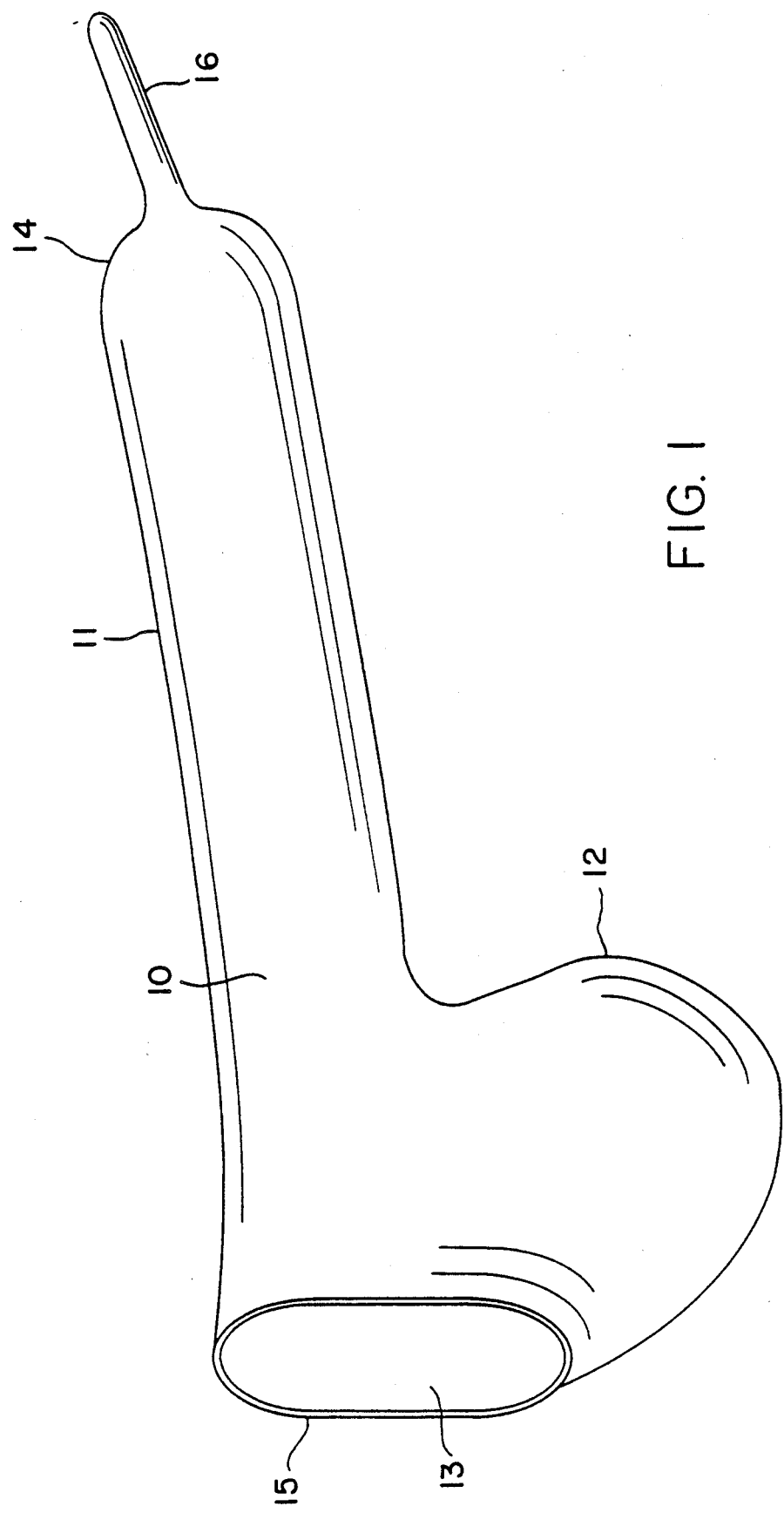
FIG. 1 is a perspective view of a first preferred embodiment of the present invention.

Referring now in detail to the drawings wherein like parts are designated by like reference numerals throughout, there is illustrated in FIG. 1 a perspective view of a first preferred embodiment of the present invention.

The first preferred embodiment is a thin walled condom device of a tubular construction that includes a single continuous elastic sheath 10. When in place over the male genitalia, a closed end 14 of the sheath 10 covers the glans penis, a shaft 11 of the sheath 10 covers the entire penis, including the base of the penis and a sack 12 of the sheath 10 covers the entire scrotum. The continuous elastic sheath 10 which includes the closed end 14, the shaft 11 and the sack 12 conforms to the general shape of the covered male genitalia. The sheath 10 further includes an open end 13.

When the sheath 10 is in place over the male genitalia, the open end 13 is bordered superiorly by the pubic region, bordered laterally by the genitocrural region and bordered posteriorly by the anterior region of the perineum. The open end 13 terminates the elastic sheath 10 at an integral elastic ring 15 of heavier construction than the sheath 10. The open end 13 is stretched against the aforementioned bordering regions of the anatomy.

A smaller diameter closed tube 16 is attached to the closed end 14 at the urethra as a receptacle for ejaculate.

The condom device is preferably made from latex rubber. The material comprising the shaft 11 preferably has a thickness ranging from 0.002 inches to 0.004 inches. A preferred diameter of the shaft 11 is 1.25 inches in the unstretched condition.

The sheath 10 is preferrably made by dipping a form into a latex rubber bath. The form is removed bearing a coating consisting essentially of latex rubber. The latex rubber coating on the form is then allowed to harden, forming the sheath 10 that conforms to the shape of the form.

According to one aspect of the present invention, venereal disease prophylaxis and contraception are achieved by providing a condom device, as described above, and positioning it over the male genitalia prior to sexual contact.

Figure 2:
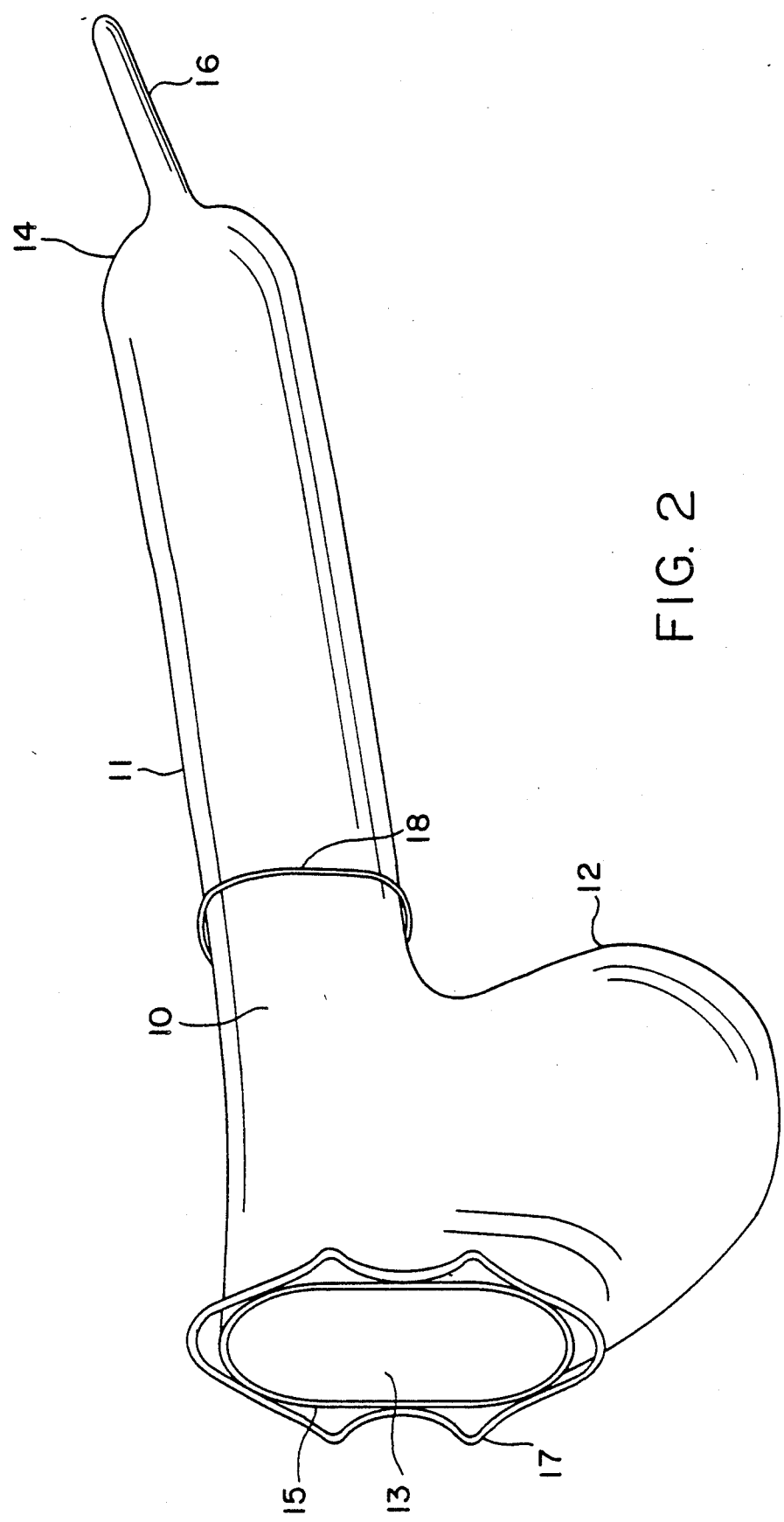
FIG. 2 is a perspective view of a second preferred embodiment of the present invention.

There is illustrated in FIG. 2 a perspective view of a second preferred embodiment of the present invention.

The second preferred embodiment is substantially similar to the first preferred embodiment except that it includes a plurality of integral handle elements 17 attached to the first elastic ring 15 and a second elastic ring 18, of heavier construction than the sheath 10, bonded to the shaft 11. The handle elements 17 are located on or grasped between the fingers and thumbs of the hands when finally placing the condom device on the male genitalia or removing the condom device from the male genitalia. The second elastic ring 18 is positioned along the shaft 11 at such a position that, when the device is in place, it is positioned at the base of the penis shaft. The second elastic ring 18 is of such a dimension that, when the device is in place, the second elastic ring 18 stretches against the base of the penis shaft.

Figure 3:
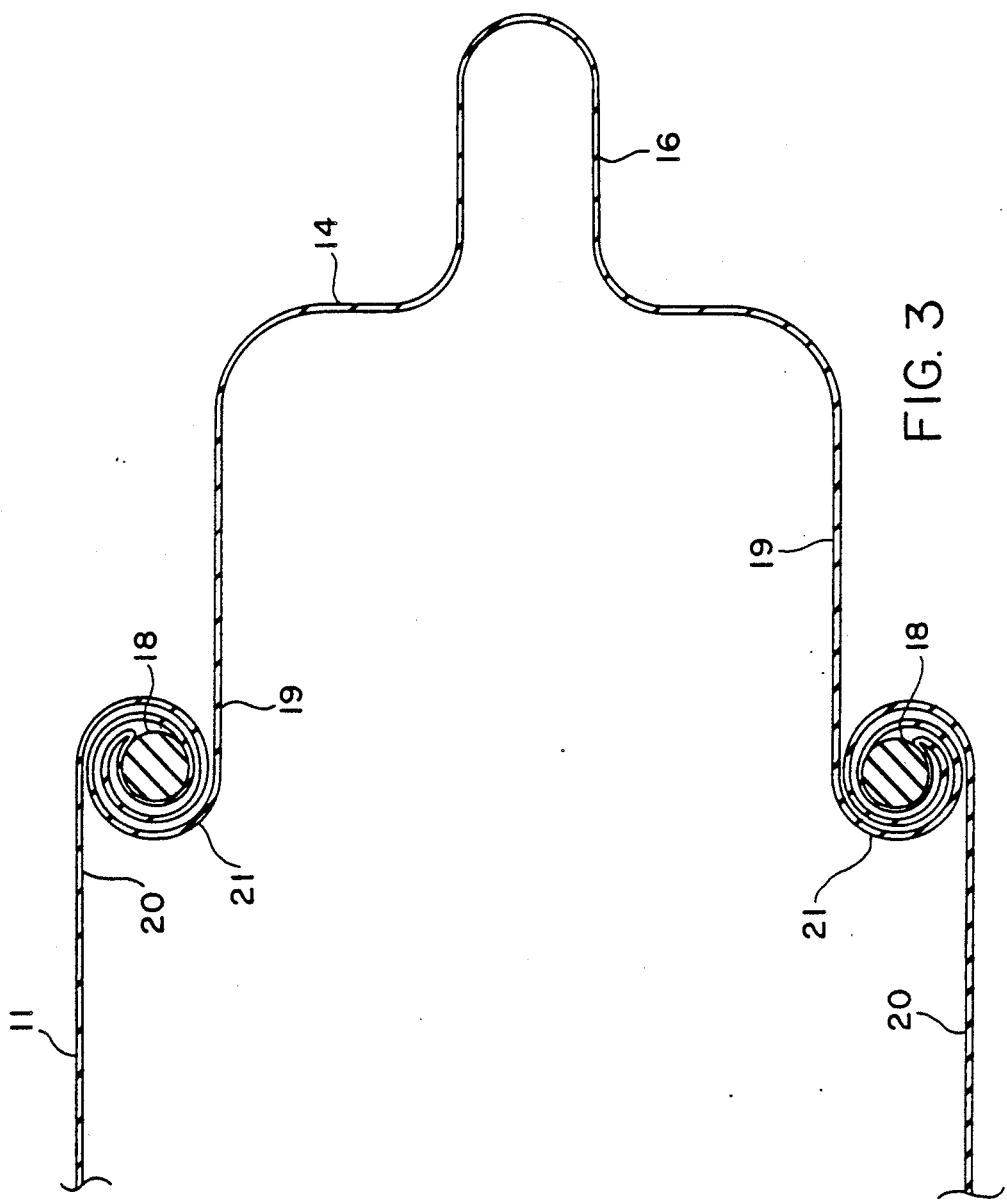
FIG. 3 is an enlarged sectional view of a segment of the second preferred embodiment, prior to complete placement of the device.

There is illustrated in FIG. 3 an enlarged sectional view of a segment of the second preferred embodiment, in a condition prior to placement of the device over the male genitalia. The sectional view shown is in a plane that includes the center axis of the shaft 11.

The shaft 11 is wound up about the second elastic ring 18 to form a generally torroidal winding. In section the torroidal winding appears as the spiral 21. The tails 20 of the spiral 21 are directed towards the open end 13 of the device and the tails 19 are directed towards the closed end 14 of the device.

According to another aspect of the present invention, venereal disease prophylaxis and contraception are achieved by providing a condom device, as described above, with shaft 11 torroidally wound about the second elastic ring 18, initially positioning the closed end 14 over the glans penis, grasping the handles 17 with the fingers and thumbs of the hand, and pulling on the handles 17 in a generally posterior direction in order to unwind the torroid and spiral 21 and finally position the condom device over the entire male genitalia prior to sexual contact. When following this procedure, the torroid and spiral 21 will unwind only to the extent as to accomodate the length of the penis of the user.

Figure 4:
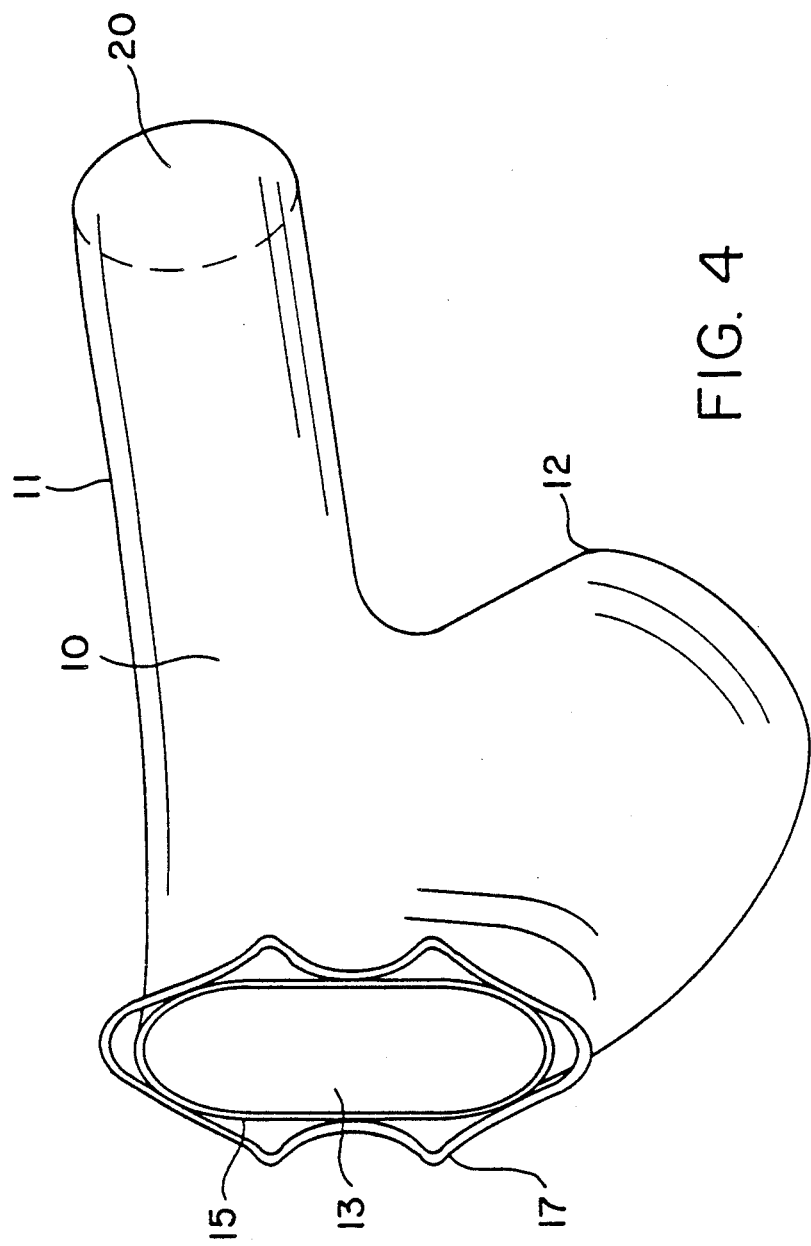
FIG. 4 is a perspective view of a third preferred embodiment of the present invention.

There is illustrated in FIG. 4 a perspective view of a third preferred embodiment of the present invention.

The third preferred embodiment is a thin walled venereal disease prophylactic device of a tubular construction that includes a single continuous elastic sheath 10. When in place over the male genitalia, a shaft 11 of the sheath 10 covers the root half of the penis shaft, including the base of the penis and a sack 12 of the sheath 10 covers the entire scrotum. The continuous elastic sheath 10, which includes the shaft 11 and the sack 12, conforms to the general shape of the covered male genitalia. The sheath 10 further includes a first open end 20 and a second open end 13.

When the sheath 10 is in place over the male genitalia, the second open end 13 is bordered superiorly by the pubic region, bordered laterally by the genitocrural region and bordered posteriorly by the anterior region of the perineum. The second open end 13 terminates the elastic sheath 10 at an integral elastic ring 15 of heavier construction than the sheath 10. The second open end 13 is stretched against the aforementioned bordering regions of the anatomy.

The third preferred embodiment may include a plurality of integral handle elements 17 attached to the elastic ring 15. The handle elements 17 are located on or grasped between the fingers and thumbs of the hands when finally placing the prophylactic device on the male genitalia or removing the prophylactic device from the male genitalia.

When the sheath 10 is in place over the male genitalia, the first open end 20 terminates the shaft 11 midway along the penis shaft. The first open end 20 is of such a dimension that, when the device is in place, the first open end 20 stretches against the penis shaft.

The third preferred embodiment is intended to be used in conjunction with a conventional, prior art, condom.

The prophylactic device is preferably made from latex rubber. The material comprising the shaft 11 preferably has a thickness ranging from 0.002 inches to 0.004 inches. A preferred diameter of the shaft 11 is 1.25 inches in the unstretched condition.

The sheath 10 is preferably made by dipping a form into a latex rubber bath. The form is removed bearing a coating consisting essentially of latex rubber. The latex rubber coating on the form is then allowed to harden, forming the sheath 10 that conforms to the shape of the form. Excess latex material is cut away and disgarded in order to form the first open end 20.

According to yet another aspect of the present invention, venereal disease prophylaxis and contraception are achieved by providing a venereal disease prophylactic device, as described above, providing a conventional, prior art, condom device that, when in place, covers the penis exclusive of the base of the penis shaft and positioning the above described prophylactic device and the conventional condom device over the male genitalia prior to sexual contact. The above described prophylactic device is preferably positioned prior to positioning the conventional condom device by initially positioning the prophylactic device about the penis shaft, grasping the handles 17 with the fingers and thumbs of the hand, and pulling the handles 17 in a generally posterior direction in order to finally position the prophylactic device over the male genitalia. The conventional condom device is then positioned over the penis in such a manner that it partially overlaps the shaft 11.

Although only preferred embodiments are specifically illustrated and described herein, it will be appreciated that many modifications and variations of the present invention are possible in light of the above teachings and within the purview of the appended claims without departing from the spirit and intended scope of the invention.

What I claim is:

1. A prophylactic and contraceptive condom device, comprising:
    a single and continuous sheath of thin walled tubular construction having a closed first end and an open second end, said sheath shaped such that, when the device is in place over the male genitalia, the sheath covers, conforms to and fits the entire erect penis, including the base of the penis shaft, and the entire scrotum, and is retained adjacent the open second end by the posterior of the scrotum;
    a ring of thicker material than the continuous sheath, bonded to said continuous sheath at such a position, that, when the device is in place over the male genitalia, said ring is substantially concentric with the penis shaft and is positioned near the base of the penis shaft, said ring partitioning said continuous sheath into a penis covering segment and a scrotum covering segment; and
    a portion of the penis covering segment being wound in combination with a portion of the scrotum covering segment about the ring into a toroidally shaped winding of more than 360 degrees, such that said ring is located at the core of said toroidally shaped winding and said penis covering segment portion and said scrotum covering segment portion are interleaved as alternate layers within said toroidally shaped winding.

2. A prophylactic and contraceptive condom device according to claim 1, wherein, when in place over the male genitalia and when at least a portion of the toroidally shaped winding is unrolled, the open second end of the continuous sheath is bordered superiorly by the pubic region, bordered laterally by the genitocrural region and bordered posteriorly by the anterior region of the perineum.

3. A prophylactic and contraceptive condom device according to claim 2, wherein, when in place over the male genitalia, the open second end is of such dimension as to stretch against the aforementioned bordering regions of the anatomy.

4. A prophylactic and contraceptive condom device according to claim 2, wherein the open second end of the continuous sheath terminates at an integral elastic ring of thicker material than the continuous sheath.

5. A prophylactic and contraceptive condom device according to claim 1, wherein the continuous sheath is comprised of an elastic material.

6. A prophylactic and contraceptive condom device according to claim 1, wherein the open second end of the continuous sheath includes a plurality of integral, attached handles.

7. A prophylactic and contraceptive condom device according to claim 1, wherein the closed first end of the continuous sheath covering the glans penis includes a smaller diameter, closed tube at the urethra as a receptacle for ejaculate.

8. A prophylactic and contraceptive condom device according to claim 1, wherein the ring is comprised of an elastic material and is of such dimension, that when the device is in place over the male genitalia and when at least a portion of the toroidally shaped winding is unrolled, said ring stretches against the penis shaft.

9. A prophylactic and contraceptive condom device according to claim 1, wherein, when the device is in place over the male genitalia and when at least a portion of the toroidally shaped winding is unrolled, the number of layers that remain taken up in the toroidally shaped winding depends upon the dimensions of the covered male genitalia.

10. A prophylactic and contraceptive condom device according to claim 1, wherein the toroidally shaped winding is wound in a direction such that the scrotum covering segment enters said winding on the outside of said winding and the penis covering segment enters said winding on the inside of said winding.

11. A method of achieving venereal disease prophylaxis and contraception comprising the steps of:
    providing, in combination:
        a single and continuous sheath of thin walled tubular construction having a closed first end and an open second end, said sheath shaped such that, when the sheath is in place over the male genitalia, the sheath covers, conforms to and fits the entire erect penis, including the base of the penis shaft, and the entire scrotum, and is retained adjacent the open second end by the posterior of the scrotum;

a ring of thicker material than the continuous sheath, bonded to said continuous sheath at such a position, that, when the sheath and the ring are in place over the male genitalia, said ring is substantially concentric with the penis shaft and is positioned near the base of the penis shaft, said ring partitioning said continuous sheath into a penis covering segment and a scrotum covering segment; and a portion of the penis covering segment being wound in combination with a portion of the scrotum covering segment about the ring into a toroidally shaped winding of more than 360 degrees, such that said ring is located at the core of said toroidally shaped winding and said penis covering segment portion and said scrotum covering segment portion are interleaved as alternate layers within said toroidally shaped winding; and positioning said continuous sheath over the male genitalia and unwinding at least a portion of the toroidally shaped winding to completely cover the entire erect penis, including the base of the penis shaft and the entire scrotum.

12. The method of achieving venereal disease prophylaxis and contraception according to claim 11, wherein the positioning step includes:

grasping a plurality of handles that are integrally attached to the open end of the continuous sheath; and pulling on said handles in a generally posterior direction in order to finally position said continuous sheath.

13. A prophylactic and contraceptive condom device, comprising:

a single and continuous sheath of thin walled tubular construction having a closed first end and an open second end, said sheath shaped such that, when the device is in place over the male genitalia, the sheath covers, conforms to and fits the entire erect penis, including the base of the penis shaft, and the entire scrotum, and is retained adjacent the open second end by the posterior of the scrotum, said sheath including a penis covering segment and a scrotum covering segment; and a portion of the penis covering segment being wound in combination with a portion of the scrotum covering segment into a toroidally shaped winding of more than 360 degrees, such that said penis covering segment portion and said scrotum covering segment portion are interleaved as alternate layers within said toroidally shaped winding.

14. A prophylactic and contraceptive condom device according to claim 13, wherein, when in place over the male genitalia and when at least a portion of the toroidally shaped winding is unrolled, the open second end of the continuous sheath is bordered superiorly by the pubic region, bordered laterally by the genitocrural region and bordered posteriorly by the anterior region of the perineum.

15. A prophylactic and contraceptive condom device according to claim 14, wherein the open second end of the continuous sheath terminates at an integral elastic ring of thicker material than the continuous sheath.

16. A prophylactic and contraceptive condom device according to claim 13, wherein the continuous sheath is comprised of an elastic material.

17. A prophylactic and contraceptive condom device according to claim 16, wherein the sheath is of such dimension, that when the device is in place over the male genitalia and when at least a portion of the toroidally shaped winding is unrolled, said toroidally shaped winding stretches against the penis shaft.

18. A prophylactic and contraceptive condom device according to claim 13, wherein the open second end of the continuous sheath includes a plurality of integral, attached handles.

19. A prophylactic and contraceptive condom device according to claim 13, wherein, when the device is in place over the male genitalia and when at least a portion of the toroidally shaped winding is unrolled, the number of layers that remain taken up in the toroidally shaped winding depends upon the dimensions of the covered male genitalia.

20. A prophylactic and contraceptive condom device according to claim 13, wherein the toroidally shaped winding is wound in a direction such that the scrotum covering segment enters said winding on the outside of said winding and the penis covering segment enters said winding on the inside of said winding.

21. A method of achieving venereal disease prophylaxis and contraception comprising the steps of:

providing, in combination:

a single and continuous sheath of thin walled tubular construction having a closed first end and an open second end, said sheath shaped such that, when the sheath is in place over the male genitalia, the sheath covers, conforms to and fits the entire erect penis, including the base of the penis shaft, and the entire scrotum, and is retained adjacent the open second end by the posterior of the scrotum, said sheath including a penis covering segment and a scrotum covering segment; and a portion of the penis covering segment being wound in combination with a portion of the scrotum covering segment into a toroidally shaped winding of more than 360 degrees, such that said penis covering segment portion and said scrotum covering segment portion are interleaved as alternate layers within said toroidally shaped winding; and positioning said continuous sheath over the male genitalia and unwinding at least a portion of the toroidally shaped winding to completely cover the entire erect penis, including the base of the penis shaft and the entire scrotum.

22. The method of achieving venereal disease prophylaxis and contraception according to claim 21, wherein the positioning step includes:

gasping a plurality of handles that are integrally attached to the open end of the continuous sheath; and pulling on said handles in a generally posterior direction in order to finally position said continuous sheath.

* * * * *